United States Patent
Koshti et al.

(10) Patent No.: US 6,531,628 B1
(45) Date of Patent: Mar. 11, 2003

(54) SUBSTANTIVE WATER-SOLUBLE 2-HYDROXY SULFOBETAINES OF CINNAMIDOALKYLAMINES

(75) Inventors: Nirmal Madhukar Koshti, Maharashtra (IN); Arun Harchandra Jawale, Maharashtra (IN); Bharat Bhikaji Parab, Maharashtra (IN); Shubhangi Dattaram Naik, Maharashtra (IN); Manasi Dattatraya Moghe, Maharashtra (IN); Tanaji Shamrao Jadhav, Maharashtra (IN); Subhash Shivling Nashte, Maharashtra (IN)

(73) Assignee: Galaxy Surfactants Ltd. (IN)

( * ) Notice: Subject to any disclaimer, the term of this patent is extended or adjusted under 35 U.S.C. 154(b) by 0 days.

(21) Appl. No.: 10/104,162

(22) Filed: Mar. 22, 2002

(30) Foreign Application Priority Data

Aug. 10, 2001 (IN) .................................... 782/MUM/2001
Sep. 28, 2001 (IN) .................................... 943/MUM/2001

(51) Int. Cl.[7] .......................................... C07C 309/14
(52) U.S. Cl. ........................... 562/44; 562/43; 510/119; 510/133
(58) Field of Search ................. 510/133, 119, 510/130, 357; 562/41, 43, 44

(56) References Cited

U.S. PATENT DOCUMENTS 3,198,815 A  *  8/1965   Mannheimer
3,547,985 A  * 12/1970   Rinkler et al.
4,218,404 A  *  8/1980   Feuer et al.
4,259,191 A  *  3/1981   Wagner
4,704,229 A  * 11/1987   Brunel et al.

* cited by examiner

Primary Examiner—Jean F. Vollano
(74) Attorney, Agent, or Firm—Pendorf & Cutliff

(57) ABSTRACT

Substantive UV-absorbing water-soluble 2-hydroxy sulfobetaine of cinnamidoalkylamines of Formula I. Hair, skin and fabric care compositions containing the compounds of Formula I.

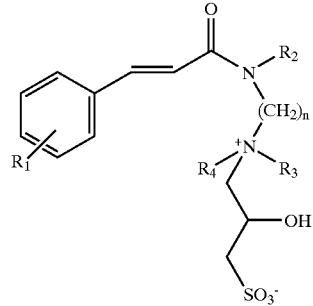

wherein, $R_1$ is a substituent, selected from H, halo, —OH, —$NH_2$, —$NO_2$, —$OCH_3$, —$N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6.

11 Claims, No Drawings

SUBSTANTIVE WATER-SOLUBLE 2-HYDROXY SULFOBETAINES OF CINNAMIDOALKYLAMINES

FIELD OF INVENTION

The invention relates to substantive water-soluble 2-hydroxy sulfobetaines of cinnamidoalkylamines. More particularly, the invention relates to novel, cationic, non-hydrolysable, non-irritating UV-absorbing sulfobetaines of cinnamidoalkylamines which are substantive to fabric, skin and hair. The invention also relates to a process of manufacture of the said compounds and further to their use in hair, skin and fabric care formulations.

BACKGROUND AND PRIOR ART

The harmful effects of solar UV-radiation on skin are well known. The UV-B (290–320 nm) portion of solar spectrum is largely responsible for erythema (sunburn) and cancer. [M. M. Rieger, Cosmet. Toiletries, 102 (3), 91, (1987); L. Taylor, Skin Cancer Foundation J., 4, (90) (1986)].

Similarly, photodegradative effect of UV-radiation on human hair is well documented. Continuous exposure to sunrays makes human hair color and makes human hair rough, brittle and difficult to comb. UV rays are reported to damage the proteins of cuticles. Prolonged irradiation results in diminished tensile strength due to breaking of disulphide bonds in keratin. [R. Beyak et al, J. Soc. Cosmet. Chem. 22, 667–668 (1971), E. Hoting et al, J. Soc. Cosmet. Chem. 46, 85–99 (1995)]

In addition, UV light is also known to fade coloured garments. [P. C. Screws, Text. Chem. Color, 11, 21 (1987); B. Milligan et al, Polym. Degrad. Stab. 10 (4), 335 (1985)]

A number of UV-absorbing compounds like derivatives of salicylic acid, benzophenones, benzotriazoles, cinnamic acid have been used in personal care products. However, all these molecules suffered from a major disadvantage of lack of substantivity. To make these UV-absorbing moieties more substantive, structural modification have been introduced.

U.S. Pat. No. 5,601,811 (1997) describes substantive UV-absorbing quaternary ammonium compounds containing cinnamidoalkylamine and product compositions for detergents, household cleaners and hair and skin personal care products. The synthesis of UV-absorbing sulphobetaines of the present invention employs sodium 3-chloro-2-hydroxy propane sulphonate to quaternize the cinnamidoalkylamines. High water solubility is desirable because these kind of substantive compounds can be formulated in oil-free compositions so that greasy feel of cosmetic preparations based on hydrophobic carrier can be avoided ! Due to their substantive nature constant reapplication of the sunscreen preparation is not necessary in activity like swimming. Hence, the compounds of the present invention are designed to address the need for highly water-soluble yet substantially substantive sunscreen molecules.

SUMMARY OF THE INVENTION

Thus the present invention provides novel, substantive, water-soluble 2-hydroxy sulfobetaines of cinnamidoalkylamines of Formula I,

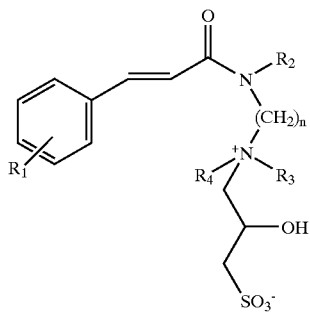

(I)

wherein, $R_1$ is a substituent, selected from H, halo, —OH, —$NH_2$, —$NO_2$, —$OCH_3$, —$N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6.

The invention further relates to a process of making a water-soluble 2-hydroxy sulfobetaines of cinnamidoalkylamines of Formula I

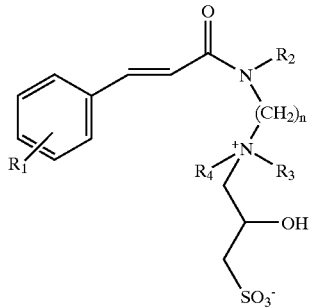

(I)

wherein, $R_1$ is a substituent, selected from H, halo, —OH, —$NH_2$, —$NO_2$, —$OCH_3$, —$N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6;

wherein, a compound of Formula II is first reacted with a compound of Formula III and the intermediate of Formula IV thus obtained is quaternised with a compound of Formula V,

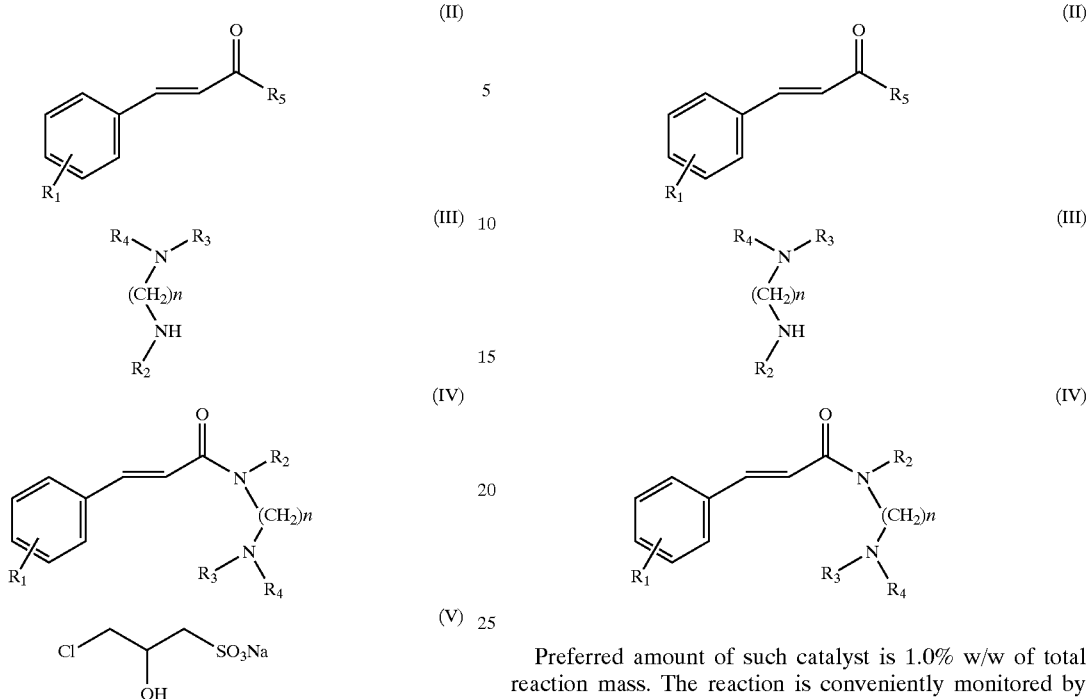

wherein in all these Formulae, $R_1$, $R_2$, $R_3$, $R_4$ and n have the same meaning as Formula I and $R_5$ of Formula II is selected form —OH, Cl⁻ or —O(CH$_2$)$_p$CH$_3$ with p=0 to 3.

In another aspect this invention provides compositions containing UV absorbing sulphobetaines that are water-soluble and substantive to skin, hair and textile fibres. The unique combination of substantivity to hair and skin, strong UV absorption and water-solubility of these 2-hydroxy sulfobetaines of cinnamidoalkylamines is very desirable for personal care products, especially for skin care applications.

DETAILED DESCRIPTION OF THE INVENTION

The UV absorbing compounds of the present invention are sulfobetaines of cinnamidoalkylamines that are prepared by reacting lower alkyl ester of cinnamic acid or acid halides of cinnamic acid with an amino compound that is subsequently quaternised with sodium 3-chloro-2-hydroxy propane sulphonate.

In the process, the amidification reaction between a compound of the Formula II when $R_5$=—OH or —O(CH$_2$)$_p$CH$_3$ (p=0 to 3), with that of Formula III is carried out at from about 120° C. to about 200° C., under pressure from about 10 psi to about 100 psi, in the presence of a basic catalyst such as sodium methoxide, sodium hydroxide from 0.25% to 5.0% by weight of the reaction mass, to afford the intermediate compound of Formula IV.

Preferred amount of such catalyst is 1.0% w/w of total reaction mass. The reaction is conveniently monitored by TLC or HPLC using UV detection. After the complete disappearance of cinnamic acid ester, the excess diamine is distilled off under vacuum.

Alternately, this reaction is carried out in the presence of a basic catalyst such as sodium methoxide, sodium hydroxide from 0.25% to 5.0% by weight of the reaction mass under atmospheric pressure, under blanket of nitrogen, with an arrangement for continuous selective removal of lower alcohol formed in the reaction.

Thus, the condensation reaction of one mole of cinnamic acid ester is carried with 1.0 to 3.0 moles of diamine at 120 to 200° C., preferably at 180° C., for 12 to 36 hours. The amines themselves can catalyse the reaction, however, the rates are found to be slower as compared with the bases like sodium methoxide and the like.

The same reaction can be performed using cinnamic acid in place of cinnamic acid ester at temperatures up to 200° C. and pressures of 100 psi, keeping the same stoichiometry (1:1.0 to 3). The excess diamine serves as solvent for the reaction.

Cinnamic acid esters and amino compounds are selected that are liquid within the disclosed temperature and pressure range.

The amidification reaction between a compound of Formula II when $R_5$=—Cl in the presence of a solvent, is carried out with that of Formula III at room temperature in the presence of solvent. The compounds of Formula IV are synthesised by reacting acid chlorides of Formula II (1.0 mole) when $R_5$ is —Cl with the diamines of Formula III (1.0 to 1.2 mole) at 20–50° C. in an inert solvent like dichloromethane, ethylene dichloride, tetrahydrofuran and the like.

In the process the cinnamidoalkylamines (Formula IV, 1 mole) are N-alkylated with sodium 3-chloro-2-hydroxy propane sulphonate quaternising agent (Formula V, 1.0 mole) in the presence of a suitable inert solvent that governs the temperature at which the reaction is carried out.

Quaternization of cinnamidoamines is carried out in solvents that include, water, lower alkanols, glycols and combinations thereof. Lower alkanols having one to four carbons atoms are suitable for use with the present

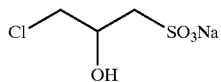
(V)

invention. Glycols having from three to eight carbon atoms are suitable for use with the present invention. Mixtures of these solvents can also be used. Solvents used are from 20 to 80% by weight of the reaction mass. The cinnamidoalkylamines (Formula IV, 1 mole) are N-alkylated with quaternising agent (Formula V, 1.0 mole) in the presence of suitable solvents preferably water, isopropanol that govern temperatures at which the reaction is carried out.

The quaternisation reaction can be conveniently done in a pressure reactor as well as in an open system. The temperatures suitable for pressure reaction range from about 60–125° C. with the pressures up to 50 psi. The pressures are governed by the amount of solvent and the temperature selected for the reaction. The conditions of reaction in an open vessel also get dictated by the choice of solvent. The reactions are usually carried out at boiling point or slightly below boiling point of the solvent employed. The resulting betaines are obtained as concentrated solutions. The progress of the reaction is monitored by measuring unquaternized amidoamine or by estimation of Cl⁻.

The number and their nature of selected substituents should not be too hydrophobic to render the final sulfobetaines water-insoluble. For purposes of the present application, water-soluble compounds are defined as being soluble in water at levels above 15% w/w. These water-soluble compounds of this invention are useful for making compositions for skin and hair care and fabric care.

The preferred sulfobetaines in accordance with the present invention form aqueous solutions at levels of at least about 15% by weight. The more preferred sulfobetaines in accordance with the present invention have a solubility of at least about 25% by weight. The most preferred compounds have a water-solubility of at least 50% w/w.

The sulfobetaines in accordance with the present invention have the structure of Formula I.

As shown in Formula I, the benzene ring preferably contains one substituent at para position $R_1$ is selected from moieties such as halo, p-OH, $-NH_2$, $-NO_2$, $-OCH_3$, $-N(CH_3)_2$.

Referring again to Formula I, the amido nitrogen is preferably is either unsubstituted ($R_2$ is hydrogen) or may contain a substituent, selected from alkyl groups containing up to 12 carbon atoms. The quaternized nitrogen of the compounds in accordance with the present invention preferably contains two substituents, $R_3$ and $R_4$, as depicted in Formula I, $R_3$ and $R_4$ are independently selected from hydrogen, benzyl and alkyl groups containing up to 6 carbon atoms.

The compounds of the present invention are sulfobetaines of cinnamidoalkylamines as shown in Formula I, in which n is an integer between 1 and 6, both inclusive. Preferred compounds in accordance with the present invention are sulfobetaines of cinnamidoalkylamines in which n is an integer between 2 and 6, both inclusive and most preferably, n of Formula I is 3.

In another embodiment the process of the present invention relates to manufacture of a compound of Formula I, namely, 3-(N-p-methoxy cinnamidopropyl, N,N-dimethyl ammonium)-2-hydroxy propane-1-sulphonate, when $R_1=-OCH_3$, $R_2=H$, $R_3=R_4=-CH_3$, and n=3, from the compounds of Formula II, namely, p-methoxy ethyl cinnamate), and Formula III, namely, N,N-dimethylpropyldiamine, to form an intermediate compound of Formula IV, namely, p-methoxy cinnamidopropyldimethyl amine and Formula V, namely, sodium 3-chloro-2-hydroxy propane sulphonate, with respective substituents $R_1$ of Formula II, $R_2$, $R_3$, $R_4$ and n of Formula III as defined for the compounds of Formula I in this embodiment, and $R_5$ of Formula II being ethoxy.

Cinnamidoalkylamine (Formula IV) are in turn synthesized by amidification of lower alkyl esters of cinnamic acid (Formula II, alkoxy group ($R_5$) may vary from $C_1$ to $C_4$) by appropriate diamines (Formula III) containing a tertiary amino group.

$R_1$, $R_2$, $R_3$ and $R_4$ of cinnamidoalkylamine (Formula IV) and the diamine (Formula III) are the same as described with respect to Formula I.

The amidification reaction is performed at temperatures up to 200° C. and pressures up to 100 psi. Accordingly, cinnamic acid esters and amino compounds are selected that are liquid within the disclosed temperature and pressure range. This reaction generates lower alcohol that need not be distilled out.

In the present invention the reaction of one mole of cinnamic acid ester is carried with 1.2 to 3 moles of diamine at 130 to 200° C., preferably at 180° C., for 12 to 36 hours. This condensation is catalysed by bases like sodium hydroxide, sodium methoxide or ethoxide, potassium hydroxide and the like. The amines themselves can catalyse the reaction, however, the rates are found to be slower as compared with the bases like sodium methoxide and the like.

From about 0.5% to 5.0% w/w of the basic catalyst should be employed. Preferred amount of such catalyst is 1.0% w/w. The reaction is conveniently monitored by TLC or HPLC using UV detection. After the complete disappearance of cinnamic acid ester the excess diamine is distilled off under vacuum.

This amidification can also be carried out under atmospheric pressure under blanket of nitrogen with an arrangement for selective condensation of the diamine and continuous removal of lower alcohol. The same reaction can be performed using cinnamic acid in place of cinnamic acid ester at temperatures up to 200° C. and pressures of 100 psi, keeping the same stoichiometry (1:1.2 to 3). The excess diamine serves as solvent for the reaction.

The sulfobetaines (Formula I) of the present invention are synthesized as concentrated solutions by N-alkylating cinnamidoamines (Formula IV) with sodium 3-chloro-2-hydroxy propane sulphonate having Formula V.

In another aspect this invention provides compositions containing quaternary ammonium compounds that are water-soluble, UV-absorbing and substantive to skin, hair and textile fibres. The hair care and skin care compositions containing compounds of Formula I can be solutions, dispersions or emulsions. The quaternary compounds of Formula I are soluble in water, alcohols, glycols, mixtures thereof, mixtures of alcohols and water and mixtures of glycols and water.

Lotions may be formed using compounds of Formula I, with or without one or more of the inert solvents like ethyl alcohol, isopropyl alcohol or propylene glycol, by combining with film forming polymers like proteins, polyvinyl pyrrolidone, polyvinyl alcohols and the like, film-forming starches and resins and the like.

Oil-in-water and water-in-oil emulsion can also be employed as vehicles to form lotions and creams. Conventional oil soluble UV-absorbing compounds like cinnamates, salicylates, p-aminobenzoates, benzophenones can be dissolved in oily phase of emulsion/lotions. The water-soluble sunscreens of the present invention are dissolved in an aqueous phase of the emulsion and combined with the oily phase using a suitable cationic emulsifier such as stearylkonium chloride.

Vegetable or mineral oils suitable for use as oil phase include mineral oil, petroleum, castor oil, sesame oil and the like. The quaternary ammonium compounds of the present invention are added to aqueous phase which is then subsequently emulsified with oily phase using an emulsifier like stearylkonium chloride or non-ionic emulsifiers like polysorbate-80, fatty alcohol ethoxylates and the like.

Perfumes, fragrances, anti-oxidants, preservatives, dyes colorants, insect repellents, fillers and suspended particulate matter, emollients, humectants, thickeners and the like may optionally be included in the sunscreen and tanning compositions of the present invention.

The sunscreen and tanning compositions of the present invention contain an effective amount of compounds of Formula I to prevent erythema. In general, an amount of about 0.5% to 10% w/w of the total composition is used. Face powder compositions of the present invention contain compounds of Formula I in an effective amount of 0.1% w/w to 0.5% w/w.

The compositions containing compounds of Formula I may contain one or more of the other cosmetic ingredients like surfactants, other sunscreen chemicals, after sun treatment materials, emollients, humectants, perfumes, antiperspirants, moisturisers, color cosmetic materials, herbal extracts, occlusive oils and essential oils.

The compositions of compound with Formula I provide hair protection from UV radiation in addition to good conditioning effect. The hair protecting preparations can be formulated in the form of creams, lotions, tonics or gels. The compounds of the present invention may also be formulated as hair care product such as shampoos, cream rinses, hair conditioners, hair dressing preparations, hair relaxers, hair coloring products and the like, capable of protecting hair from UV-B radiation.

The rinse-off preparations like shampoos, face washes and bathing bars contain 0.5 to 8.0% w/w of compounds of Formula I. It may be noted that these betaines are compatible with usual anti-dandruff, anti-microbial agents like Zinc pyrithione, Irgasan, Pyroctone. Hence, these compounds of Formula I can be incorporated in anti-dandruff shampoos.

The compounds of Formula I are completely compatible with anionic surfactants like sodium lauryl ether sulphate due to its zwittwerionic nature. The transparent shampoo formulation based on sodium lauryl ether sulphate has been shown to deposit the UV-absorbing betaine compounds on hair (Example III).

The cream hair conditioner is an example of emulsion type with both water-soluble and water-insoluble sunscreens is given in Example IV.

Soap bars, both opaque and transparent/translucent can be formulated with compounds of UV-absorbing compounds of Formula I. In soap bars, the sulfobetaines of cinnamidoalkylamines can be incorporated from 0.5 to 10.0% w/w, more preferably from 1.0 to 2.0% w/w of total composition. It may be noted that the compounds of Formula I in the following combi-bar formulation are compatible with anionic surfactants (Example V).

For everyday use a sunscreen cream to protect the skin from both UV-A and UV-B radiation can be formulated as given in Example VI. The substantive UV absorbers, both water-insoluble and water-soluble (compounds of Formula I) can be conveniently incorporated at 2.0% each w/w of total composition. To cover UV-A range butyl methoxy dibenzoyl methane (Parsol 1789) is incorporated.

Furthermore, the compounds of Formula I of the present invention can be effectively incorporated into typical detergent powder and household cleaning product compositions to impart anti-fading effect to colored fabric through substantivity. Typical detergent and household cleaning product compositions in accordance with the present invention include one or more surfactants, selected from anionic, cationic, nonionic and amphoteric detergents, alone or in combination. A typical detergent powder has been shown to deposit zwitter ionic photofilters of the present invention on fabric (Example VII).

The hair and skin protecting and detergent and household cleaning compositions of the present invention are also formed by admixing, dissolving the compounds of Formula I into the desired cosmetically acceptable diluent and carrier. The preferred cosmetic compositions are solutions, dispersions or emulsions. The compositions contain an effective amount of one or more of UV-absorbing and conditioning compounds of the present invention to prevent erythema and darkening of skin due to solar damage.

In general, an amount of about 0.5% to about 10% w/w and preferably between 2.5 to 8.0% w/w of total cosmetic composition of compounds of Formula I are useful in personal hair and skin care products, sunscreens and tanning lotions. Typically, the ingredients are combined with mixing and heating if necessary until a uniform, homogeneous product is formed. With respect to the emulsion products of the present invention, the water-soluble and water-insoluble ingredients are mixed together separately and combined with suitable emulsifier, preferably a cationic emulsifier, to form an emulsion.

Finally, the substantive UV-B absorbers of the present invention are non-hydrolysable and contain the most widely used chromophore of cinnamido moiety for UV absorption. A representative substantive sulfobetaines of cinnamidoalkylamines of the present invention, 3-(N-p-methoxy cinnamidopropyl, N,N-dimethyl ammonium)-2-hydroxy propane-1-sulphonate, has molar extinction coefficient, $\in$ of 24,000. It is non-irritant and non-mutagenic (Ames test). High water-solubility coupled with substantivity of the compounds of the present invention, is very much desired in cosmetic formulations without an oily phase.

EXAMPLES

The invention will now be illustrated with the help of examples, Examples I and II for process and Examples III to VII for compositions. The examples are by way of illustrations only and in no way restrict the scope of invention. Many changes and modifications can be made within the scope of the invention without departing with spirit thereof and the invention includes all such modifications. A few formula variations for the preparation of shampoo, cream hair conditioner, transparent bathing bar, sunscreen cream and detergent powder with compounds of Formula I are illustrated in Examples III, IV, V, VI and VII respectively.

Example I

Epichlorohydrin was obtained from TamilNadu Petro Products, Chennai. N,N-ditnethyl propyldiamine and sodium sulphite were obtained from BASF and Thai Sulphate Ltd. respectively. Ethyl p-methoxy cinnamate was supplied by Galaxy Surfactants Ltd.

Process for Preparation 3-(N-p-Methoxy Cinnamidopropyl, N,N-Dimethyl Ammonium)-2-hydroxy Propane-1-sulphonate The compound of Formula I, wherein, $R_1$=—$OCH_3$; $R_2$=—H; $R_3$=$R_4$=$CH_3$; n=3. p-Methoxy cinnamidopropyldimethylamine was synthesised from ethyl p-methoxy cinnamate and N,N-dimethylpropyldiamine.

a) Preparation of p-methoxy Cinnamidopropyldimethylamine:

Ethyl p-methoxy cinnamate (206.0 g, 1.0 mole), N,N-dimethylpropyldiamine (306.0 g, 3.0 mole) and sodium methoxide (2.0 g) were charged in a pressure reactor. The air inside the reactor was flushed out by purging of nitrogen. The reaction mixture was then stirred at 180° C. (this generated pressure of 18 kg/cm$^2$) for 36 hours. The progress of reaction was monitored by disappearance of ethyl p-methoxy cinnamate on chromatography (TLC and HPLC). The TLC was performed on aluminium coated silica gel plates (Merck-60-F-254) and viewed with a UV lamp at 254 nm. HPLC was performed using reversed phase technique on a C-18 bonded (octadecyl silane) column and 60% aqueous methanol as mobile phase (1.0 ml/min) and detection at 280 nm. The excess amine was removed under vacuum. The golden yellow solid (263.0 g) thus obtained had amine value of 245. Molar extinction coefficient, ∈, in methanol was found to be 24,224 at 290 nm. IR in dichloromethane showed carbonyl stretching of amide at 1660 cm$^{-1}$ and NH stretching at 3300 cm$^{-1}$.

$^1$H NMR (300 MHz, CDCl$_3$): δ 1.73 (p, 2H, J=6.6 Hz), 2.26 (s, 6H), 2.42 (t, 2H, J=6.6 Hz),3.45 (q, 2H, J=6.0 Hz), 3.81 (s, 3H), 6.27 (d, 1H, J=15.6 Hz), 6.86 (d, 2H, J=8.7 Hz), 7.43 (d, 2H, J=8.7 Hz), 7.53 (d, 1H, J=15.6 Hz).

$^{13}$C NMR (125 MHz, CDCl$_3$): δ 14.10, 21.27, 22.69, 26.35, 29.23, 29.34, 29.51, 29.64, 31.93, 36.38, 50.67, 55.24, 62.47, 64.24, 114.10, 119.43, 125.83, 127.92, 128.89, 129.47, 139.56, 143.87, 160.67, & 167.25.

b) Preparation of Sodium 3-chloro-2-hydroxy Propane Sulphonate:

It was prepared as per the procedure described in U.S. Pat. No. 2,129,264 (1938). To a stirred mixture of sodium bisulphite (294.0 g, 2.83 moles) and sodium sulphite (84.0 g, 0.67 moles) in water (514 ml), epichlorohydrin (250.0 g, 2.70 moles) was added dropwise maintaining the temperature of reaction mass below 20° C. over a period of 6 hours. The reaction mass was cooled to 5° C. and the precipitated white solid was filtered and dried at 100° C. to yield 424.0 g (82%) of sodium salt of 3-chloro-2-hydroxy propane sulphonic acid.

c) Preparation of 3-(N-p-Methoxy Cinnamidopropyl, N,N-Dimethyl Ammonium)-2-hydroxy Propane-1-sulphonate:

p-Methoxy cinnamidopropyldimethyl amine (482.0 g, 1.84 moles) was charged in a stainless steel pressure reactor along with sodium 3-chloro-2-hydroxy propane sulphonate (397.0 g, 2.02 moles) and water (879 ml). The reaction mixture was stirred under nitrogen pressure of 0.5 kg/cm$^2$ at 85–90° C. The reaction was monitored by estimation of either Cl$^-$ or unreacted cinnamidoalkylamine. The reaction was continued till the stoichiometric quantity of Cl$^-$ was liberated to yield 1758 g of pale yellow coloured aqueous solution having solid content of 50.0% and NaCl of 6.12%.

IR (KBr): 1650 cm$^{-1}$, 3300–3400 cm$^{-1}$. $^1$H NMR (D$_2$O, 300 MHz): δ 2.05 (m, 2H), 3.10–3.17 (m, 8H), 3.31–3.36 (t, 2H), 3.41–3.64 (m, 5H), 3.78 (s, 3H), 4.60–4.67 (m, 1H), 6.34 (d, 1H, J=15 Hz), 6.91 (d, 2H, J=9 Hz), 7.34 (d, 1H, J=15 Hz), 7.45 (d, 2H, J=9 Hz).

The molar extinction coefficient, ∈ was found to be 24,000 at λmax 306 nm in water.

The final compound was analysed on HPLC using ion-pairing technique. The mobile phase employed for ion-pairing comprised of 0.1 M sodium octane sulphonic acid in aqueous methanol (50:50). Reversed phase column Chromspher C8 was used with mobile phase flow rate of 0.5 ml/min. The detection was done at 280 nm. The retention time for 3-(N-p-methoxy cinnamidopropyl, N,N-dimethyl ammonium)-2-hydroxy propane-1-sulphonate was found to be 2.08 minutes.

The purity of final compound from this analysis was found to be 98.0% with 2.0% unquaternised amine.

Example II

Process for Preparation 3-(N-p-Methoxy Cinnamidopropyl, N,N-Dimethyl Ammonium)-2-hydroxy Propane-1-sulphonate The compound of Formula I, wherein, $R_1$=—$OCH_3$; $R_2$=—H; $R_3$=$R_4$=$CH_3$; n=3; $R_5$=—$C_{12}H_{25}$.

p-Methoxy cinnamidopropyldimethylamine was synthesised from p-methoxy cinnamoyl chloride and N,N-dimethylpropyldiamine.

(a) Preparation of p-Methoxy Cinnamoyl Chloride:

To a stirred suspension of p-methoxy cinnamic acid (178.0 g, 1.0 mole) in dichloromethane (500 ml), thionyl chloride (238.0 g, 2.0 moles) was added slowly and the reaction mass was heated at 45° C. for 3 hours. The excess of thionyl chloride was removed under vacuum and the p-methoxy cinnamoyl chloride was distilled (145° C./0.2 mm) in 85% yield as colourless solid with m.p. 50° C. (Literature m.p. 50° C., Dictionary of Organic Compounds, Chapmann and Hall, 1994).

(b) Preparation of p-Methoxy Cinnamidopropyldimethylamine:

To a stirred solution of N,N-dimethylpropyldiamine (102.0 g, 1.0 mole) in dichloromethane (500 ml), solution of p-methoxy cinnamoyl chloride (196.0 g, 1.0 mole) in dichloromethane from step (a) was slowly added and the reaction was continued at room temperature for 2 hours. The reaction mixture in dichloromethane was washed with aqueous sodium hydroxide (200 ml, 20.0%). The organic layer was dried over anhydrous sodium sulphate. The removal of solvent using a rotary evaporator afforded the p-methoxy cinnamidopropyldimethylamine (235.0 g) as colourless solid, m.p. 80° C. Reversed phase HPLC showed it to be 98% pure with amine value 217.

The NMR, IR and HPLC data matched with the data for the compound obtained in Example I(b).

(c) Preparation of 3-(N-p-Methoxy Cinnamidopropyl, N,N-Dimethyl Ammonium)-2-hydroxy Propane-1 -sulphonate:

The preparation was carried out as per the experiment described in Example I(c).

The NMR, IR, UV data matched with the data obtained in Example I(c).

Example III

Preparation of Transparent Shampoo

A shampoo composition containing 3-(N-p-methoxy cinnamidopropyl, N,N-dimethyl ammonium)-2-hydroxy propane-1-sulphonate of Example I was prepared in accordance with the optimum formulation given below. Acceptable formula variations for the preparation of such shampoo are also illustrated.

| Ingredient | Range % (w/w) | Preferred % (w/w) | Optimum % (w/w) |
|---|---|---|---|
| SLES-2 (30%) | 40–60 | 45–60 | 50.00 |
| CAPB (30%) | 1–10 | 2–10 | 8.00 |
| 3-(N-p-methoxy cinnamidopropyl, N,N-dimethyl ammonium)-2-hydroxy propane-1-sulphonate | 0.5–10 | 2–5 | 2.00 |
| Galsilk | 3–10 | 4–6 | 5.00 |
| Chelating agents/sodium chloride/ preservatives/colour and fragrances | Quantity sufficient | | |
| Deionised water | Quantity sufficient to make 100% | | |

A clear shampoo was formulated using 3-(N-p-methoxy cinnamidopropyl, N,N-dimethyl ammonium)-2-hydroxy propane-1-sulphonate prepared as in Example I. The other active ingredients, SLES-2, Sodium lauryl ether sulphate, an anionic surfactant, 30% aqueous solution, CAPB, Cocoamidopropyl betaine, an amphoteric surfactant, 30% aqueous solution and Galsilk, Polyquaternium-7 were obtained from Galaxy Surfactants Ltd., Mumbai, India. Methyl paraben and propyl paraben were obtained from Gayatri Laboratories, Mumbai, India. Approved fragrances and colors were obtained from S. H. Kelkar & Co., Mumbai, India and Koel Colors Pvt. Ltd., Mumbai, India respectively.

The transparent shampoo was prepared as follows:

The major ingredients were mixed with heating to 50° C. until a uniform homogeneous mixture was formed. The resulting mixture was then cooled to room temperature with continuous stirring. The required chelating agent, colour, perfume were added. The viscosity was adjusted to 2500 cps with sodium chloride.

The 3-(N-p-methoxy cinnamidopropyl, N,N-dimethyl ammonium)-2-hydroxy propane-1-sulphonate was found to be completely compatible with anionic surfactant. The substantivity experiment was performed as described under;

Virgin hair (5.0 g) were washed with 10% SLES solution and rinsed with plain water. The tresses were treated for exactly 5.0 minutes with clear shampoo (containing 2.0% of 3-(N-p-methoxy cinnamidopropyl, N,N-dimethyl ammonium)-2-hydroxy propane-1-sulphonate) as described in Example I that was diluted five times with water. After the treatment the tresses were washed thoroughly with copious amount of water. The adsorbed UV-absorbing sulphobetaine was extracted from the hair surface by immersing each tress in isopropanol at 65° C. for 30 minutes. A known volume of this isopropanol/sulfobetaine mixture was analysed by UV-spectroscopy to determine its absorption intensity.

The substantivity was found to be 28 mg/100 g of hair.

Example IV
Preparation of Cream Hair Conditioner

A cream hair conditioner containing 3-(N-p-methoxy cinnamidopropyl, N,N-dimethyl ammonium)-2-hydroxy propane-1-sulphonate of Example I was prepared in accordance with the optimum formulation given below. Acceptable formula variations for the preparation of such cream hair conditioner are also illustrated.

| Ingredient | Range % (w/w) | Preferred % (w/w) | Optimum % (w/w) |
|---|---|---|---|
| 3-(N-p-methoxy cinnamidopropyl, N,N-dimethyl ammonium)-2-hydroxy propane-1-sulphonate | 0.5–5 | 1–3 | 2.0 |
| Cocoamidopropyl betaine | 1–6 | 0.5–2 | 0.5 |
| Cetyl trimethyl ammonium chloride | 1–15 | 4–10 | 4.5 |
| Cetostearyl alcohol | 1–15 | 5–10 | 5.5 |
| Lanoline | 0.5–10 | 1–5 | 1.5 |
| Isopropyl myristate | 0.5–5 | 1–3 | 1.0 |
| Chelating agents/preservatives/ fragrance | Quantity sufficient | | |
| Deionised water | Quantity sufficient to make 100% | | |

Cetyltrimethylammonium chloride was obtained from Flame Pharmaceuticals Pvt. Ltd., Mumbai, India, Isopropyl myristate was obtained from Anusynth Chemical Industries, Mumbai, India, Lanoline was obtained from Rolex Lanoline Products Ltd., Mumbai, India. Phenoxyethanol was obtained from Galaxy Surfactants Ltd., Mumbai, India.

The cream hair conditioner was prepared as follows:

Aqueous phase containing cetyltrimethylammonium chloride, cocoamidopropyl betaine, 3-(N-p-methoxy cinnamidopropyl, N,N-dimethyl ammonium)-2-hydroxy propane-1-sulphonate and water were stirred together at 70° C. Oily phase comprising cetostearyl alcohol, isopropyl myristate, lanoline and preservatives was maintained at 70° C. under stirring. The oily phase is slowly added to the stirred aqueous phase at 70° C. and the whole mixture was cooled under vigorous stirring to 40° C. Perfume and other additives were added and continued cooling under stirring to get good cream.

Example V
Preparation of Transparent Bathing Bar

A transparent bathing bar containing 3-(N-p-methoxy cinnamidopropyl, N,N-dimethyl ammonium)-2-hydroxy propane-1-sulphonate of Example II was prepared in accordance with the optimum formulation given below. Acceptable formula variations for the preparation of such transparent bathing bar are also illustrated.

| Ingredient | Range % (w/w) | Preferred % (w/w) | Optimum % (w/w) |
|---|---|---|---|
| SLES (30%) | 10–50 | 20–35 | 28 |
| CAPB (30%) | 5–30 | 10–20 | 16 |
| Sodium cocoate | 5–20 | 10–15 | 9.0 |
| Sodium stearate | 15–70 | 15–20 | 13.8 |
| Propylene Glycol | 10–30 | 10–25 | 20 |
| Sorbitol (70%) | 4–15 | 8–10 | 8.0 |
| 3-(N-p-methoxy cinnamidopropyl, N,N-dimethyl ammonium)-2-hydroxy propane-1-sulphonate | 0.5–10 | 1.0–5.0 | 2.0 |
| Chelating agent/colour and fragrance | Quantity sufficient | | |
| Deionised water | Quantity sufficient to make 100% | | |

The transparent bathing bar was prepared as follows:

All ingredients were heated together under stirring to 70° C. till the reaction mass became homogenous and transparent. The reaction mass was cooled to 40° C. and the required amounts of chelating agents, perfume and colour were added. The molten mass was cast in moulds of desired shape to yield transparent bathing bar. It could be easily seen that the transparency of bathing bar was unaffected proving the total compatibility of 3-(N-p-methoxy cinnamidopropyl, N,N-dimethyl ammonium)-2-hydroxy propane-1-sulphonate with anionic surfactant.

The transparent bar thus made was evaluated as per the procedure described in Example III and the substantivity was found to be 27 mg/100 g of hair.

Example VI

Preparation of Sunscreen Cream

A sunscreen cream for every day use containing 3-(N-p-methoxy cinnamidopropyl, N,N-dimethyl ammonium)-2-hydroxy propane-1-sulphonate of Example I was prepared in accordance with the optimum formulation given below. Acceptable formula variations for the preparation of such sunscreen cream are also illustrated.

| Ingredient | Range % (w/w) | Preferred % (w/w) | Optimum % (w/w) |
|---|---|---|---|
| 3-(N-p-methoxy cinnamidopropyl, N,N-dimethyl ammonium)-2-hydroxy propane-1-sulphonate | 1–10 | 1–5 | 2.0 |
| Octyl methoxy cinnamate | 1–10 | 1–5 | 2.0 |
| Parsol-1789 (UV-A filter) | 1–5 | 1–3 | 1.0 |
| Polysorbate-80 (Tween-80) | 1–12 | 3–7 | 5.0 |
| Lauryl alcohol ethoxylate - 9 EO | 1–12 | 3–7 | 5.0 |
| Liquid paraffin oil | 1–12 | 3–7 | 5.0 |
| Isopropyl myristate | 1–12 | 3–7 | 5.0 |
| Ethylene glycol monostearate | 1–12 | 3–7 | 5.0 |
| Glyceryl monostearate | 1–12 | 3–7 | 5.0 |
| Cetostearyl alcohol | 1–12 | 3–7 | 5.0 |
| Dimethicone copolyol | 1–10 | 2–3 | 2.0 |
| Vitamin E acetate | 0.5–5 | 1–3 | 0.5 |
| Niacinamide | 0.5–5 | 1–3 | 1.0 |
| Hydroquinone | 0.5–3 | 1–2 | 1.0 |
| Sodium sulphite | 0.1–1 | 0.1–0.5 | 0.2 |
| Preservatives/fragrance | Quantity sufficient | | |
| Deionised water | Quantity sufficient to make 100% | | |

Parsol—1789 was procured from Givaudan, Roure, USA. Tween-80, Niacinamide and Vitamin E acetate were obtained from S. D. Fine Chem., Mumbai, India. Lauryl alcohol ethoxylate, ethylene glycol monostearate, glyceryl monostearate and octyl methoxy cinnamate were obtained from Galaxy Surfactants Ltd., Mumbai, India. Dimethicone copolyol (SF 1188A) was obtained from General Electric, Bangalore, India.

The sunscreen cream was prepared as follows:

Aqueous phase containing 3-(N-p-methoxy cinnamidopropyl, N,N-dimethyl ammonium)-2-hydroxy propane-1-sulphonate, Tween-80, lauryl alcohol ethoxylate-9 EO, sodium sulphite, dimethicone copolyol and water was stirred at 70° C. The oily phase comprising of octyl methoxy cinnamate, isopropyl myristate, paraffin oil, glyceryl monostearate, ethylene glycol monostearate, Vitamin E acetate, cetostearyl alcohol, niacinamide, hydroquinone and the preservatives was heated under stirring to 70° C. The oily phase is then added to the vigorously stirred aqueous phase and cooled under stirring to 40° C. At this stage fragrances were added and cooled under stirring to room temperature to get a good shiny cream.

Example VII

Preparation of Detergent Powder

A detergent powder containing 3-(N-p-methoxy cinnamidopropyl, N,N-dimethyl ammonium)-2-hydroxy propane-1-sulphonate of Example I was prepared in accordance with the optimum formulation given below. Acceptable formula variations for the preparation of such detergent powder are also illustrated.

| Ingredient | Range % (w/w) | Preferred % (w/w) | Optimum % (w/w) |
|---|---|---|---|
| Soda ash | 20–50 | 20–30 | 20 |
| Sodium tripolyphosphate | 1–30 | 15–25 | 25 |
| Sodium alkyl benzene sulphonate | 10–50 | 10–30 | 20 |
| Sodium chloride | 1–45 | 5–15 | 5.0 |
| Sodium sulphate | 1–40 | 10–20 | 20 |
| 3-(N-p-methoxy cinnamidopropyl, N,N-dimethyl ammonium)-2-hydroxy propane-1-sulphonate | 0.5–10 | 2–4 | 2.0 |
| Sodium carboxy methyl cellulose | 0.5–5 | 1–2 | 1.0 |
| Sodium silicate | 1–5 | 1–2 | 2.0 |
| Chelating agent/colour and fragrances | Quantity sufficient | | |

Linear alkyl benzene sulphonic acid was obtained from Albright and Wilson Chemicals (India) Ltd., Mumbai, India The detergent powder was prepared as follows:

To a stirred mixture of soda ash, sodium tripolyphosphate, sodium chloride and sodium sulphate, linear alkyl benzene sulphonic acid was slowly added. The mixture was then cooled to room temperature. Other active ingredients including sodium carboxy methyl cellulose, sodium silicate and 3-(N-p-methoxy cinnamidopropyl, N,N-dimethyl ammonium)-2-hydroxy propane-1-sulphonate were then added to this mixture along with the other additives like nonionic surfactant, bleaching agent, optical brightener, chelating agent, colour and perfume and stirring was continued to get uniform detergent powder.

The detergent thus made was evaluated for the deposition of quaternary on cotton fabric (substantivity) as per the principles described in Example III and was found to be 12 mg/100 g of cotton fabric.

What is claimed is:

1. A water-soluble 2-hydroxy sulfobetaines of cinnamidoalkylamines of Formula I

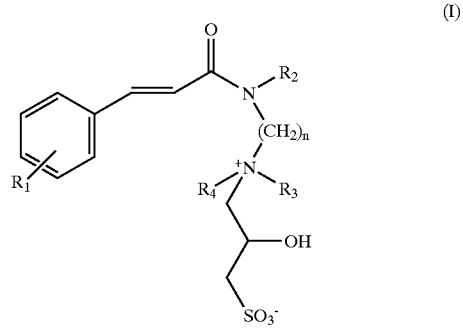

wherein, $R_1$ is a substituent, selected from H, halo, —OH, —NH$_2$, —NO$_2$, —OCH$_3$, —N(CH$_3$)$_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6.

2. A quaternary salt of claim 1, wherein the salt is 3-(N-p-methoxy cinnamidopropyl, N,N-dimethyl ammonium)-2-hydroxy propane-1-sulphonate, wherein, $R_1$=para —OCH$_3$, $R_2$=—H, $R_3$=$R_4$=—CH$_3$ and n=3.

3. A process of making a water-soluble 2-hydroxy sulfobetaines of cinnamidoalkylamines of Formula I

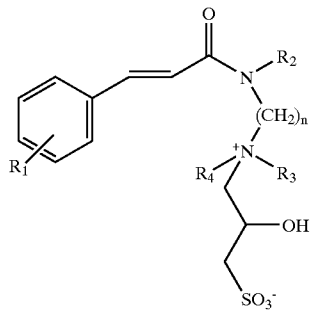

(I)

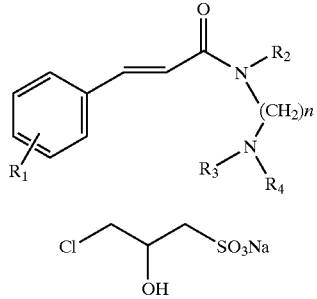

(IV)

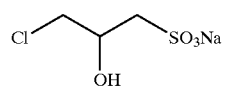

(V)

wherein, $R_1$ is a substituent, selected from H, halo, —OH, —$NH_2$, —$N_{O2}$, —$OCH_3$, —$N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6;

wherein, a compound of Formula II is first reacted with a compound of Formula III to produce an intermediate of Formula IV which is quaternised with a compound of Formula V to provide the compound of Formula I

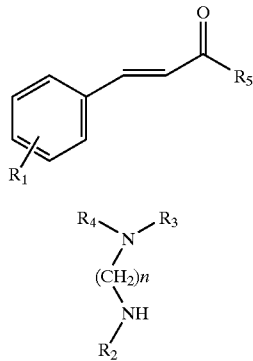

(II)

(III)

wherein in all the formulae, $R_1$, $R_2$, $R_3$, $R_4$ and n have the same meaning as Formula I and $R_5$ of Formula II is selected form —OH, —Cl, or —$O(CH_2)_pCH_3$ with p=0 to 3.

4. A composition comprising a sulfobetaine of claim 1 and one or more of other cosmetic ingredients selected from the group consisting of aqueous and oily moisturisers, film forming agents, emulsifiers, thickening agents, skin and hair conditioning agents, humectants, vegetable oils, surfactants, emollients and rheological modifiers.

5. The composition of claim 4, further comprising a detergent selected from the group consisting of anionic detergents, cationic detergents, non-ionic detergents, amphoteric detergents, and combination thereof.

6. The composition of claim 4, wherein said water-soluble 2-hydroxy sulfobetaine of cinnamidoalkylamine is present in an amount in the range from about 0.5% to about 10.0% w/w of said composition.

7. The composition of claim 4, wherein the composition is incorporated into a shampoo formulation.

8. The composition of claim 4, wherein the composition is incorporated into a hair conditioner formulation.

9. The composition of claim 4, wherein the composition is incorporated into a bathing bar formulation.

10. The composition of claim 4, wherein the composition is incorporated into a sunscreen cream formulation.

11. The composition of claim 4, wherein the composition is incorporated into a detergent powder formulation.

* * * * *